(12) United States Patent
Choi

(10) Patent No.: US 11,701,401 B2
(45) Date of Patent: Jul. 18, 2023

(54) HERBAL COMPOSITION IN POWDER, PILL OR LIQUID FORM FOR SPEEDING UP FRACTURE HEALING AND BONE REGENERATION AND HERBAL FORMULATION IN POWDER, PILL OR LIQUID FORM CONTAINING THE SAME

(71) Applicant: Young Jin Choi, Seoul (KR)

(72) Inventor: Young Jin Choi, Seoul (KR)

( * ) Notice: Subject to any disclaimer, the term of this patent is extended or adjusted under 35 U.S.C. 154(b) by 84 days.

(21) Appl. No.: 17/692,579

(22) Filed: Mar. 11, 2022

(65) Prior Publication Data

US 2023/0023078 A1 Jan. 26, 2023

(30) Foreign Application Priority Data

Jul. 22, 2021 (KR) ........................ 10-2021-0096593

(51) Int. Cl.
*A61P 19/08* (2006.01)
*A61K 36/8984* (2006.01)
(Continued)

(52) U.S. Cl.
CPC .......... *A61K 36/8984* (2013.01); *A61K 35/32* (2013.01); *A61K 36/21* (2013.01);
(Continued)

(58) Field of Classification Search
CPC ....... A61P 19/08; A61K 36/21; A61K 36/232; A61K 36/481; A61K 36/8984;
(Continued)

(56) References Cited

FOREIGN PATENT DOCUMENTS

CN 101721580 A * 6/2010
KR 2005050291 A * 5/2005
(Continued)

OTHER PUBLICATIONS

Frank Qiang Fu, Mingshu Xu, Zhijiang Wei and Weidong Li, Biostudy on Traditional Chinese Medicine Massa Medicata Fermentata, 2020, ACS Omega, vol. 5, pp. 10987-10994 (Year: 2020).*
(Continued)

*Primary Examiner* — David W Berke-Schlessel
*Assistant Examiner* — Trent R Clarke
(74) *Attorney, Agent, or Firm* — Harvest IP Law, LLP

(57) ABSTRACT

The present invention relates to an herbal composition in powder, pill or liquid form for speeding up fracture healing and bone regeneration, which may promote fracture healing and bone regeneration by containing medicinal herbs capable of improving fracture healing and bone regeneration and medicinal herbs capable of enhancing digestion and absorption, and an herbal formulation in powder, pill or liquid form containing the same. The herbal composition in powder, pill or liquid form for speeding up fracture healing and bone regeneration according to the present invention contains 20 parts by weight of *Angelica gigas*, 16 parts by weight of *Dendrobium moniliforme*, 12 parts by weight of *Dipsaci radix*, 10 parts by weight of antler, 8 parts by weight of *Cnidium officinale*, 8 parts by weight of *Astragalus membranaceus*, 4 parts by weight of *Achyranthes japonica*, and 4 parts by weight of *Massa medicata fermentata*.

4 Claims, 16 Drawing Sheets

(51) Int. Cl.
  *A61K 36/232* (2006.01)
  *A61K 36/35* (2006.01)
  *A61K 35/32* (2015.01)
  *A61K 36/234* (2006.01)
  *A61K 36/21* (2006.01)
  *A61K 36/282* (2006.01)
  *A61K 36/704* (2006.01)
  *A61K 36/28* (2006.01)
  *A61K 36/481* (2006.01)

(52) U.S. Cl.
  CPC .......... *A61K 36/232* (2013.01); *A61K 36/234* (2013.01); *A61K 36/28* (2013.01); *A61K 36/282* (2013.01); *A61K 36/35* (2013.01); *A61K 36/481* (2013.01); *A61K 36/704* (2013.01); *A61P 19/08* (2018.01)

(58) Field of Classification Search
  CPC .... A61K 35/32; A61K 36/234; A61K 36/282; A61K 36/704; A61K 36/70
  See application file for complete search history.

(56) References Cited

FOREIGN PATENT DOCUMENTS

| KR | 10-0684916 | 2/2007 |
| KR | 10-0731160 | 6/2007 |
| KR | 10-2019-0135652 | 12/2019 |
| KR | 10-2020-0033241 | 3/2020 |

OTHER PUBLICATIONS

"Japanese chaff flower" is a pdf of the webpage from the invasive plant atlas accessible at https://www.invasiveplantatlas.org/subject.html?sub=14211 accessed on Jun. 15, 2022, available online Oct. 2018 according to webpage (Year: 2018).*
English Specification of 10-0731160.
English Specification of 10-2020-0033241.
English Specification of 10-2019-0135652.
English Specification of 10-0684916.

* cited by examiner

* A: Fracture line

\* A : Fracture line

* A : Fracture line

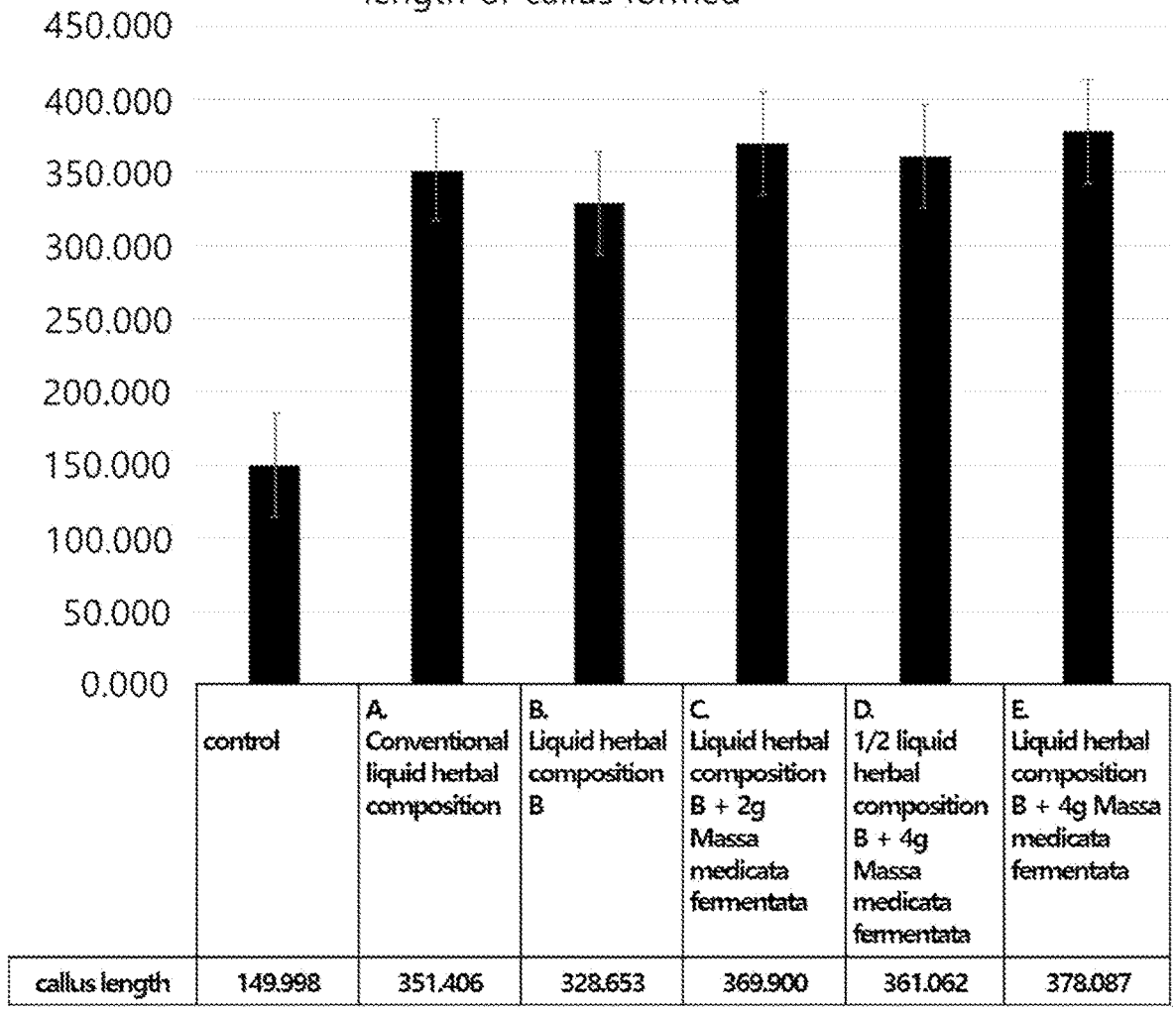

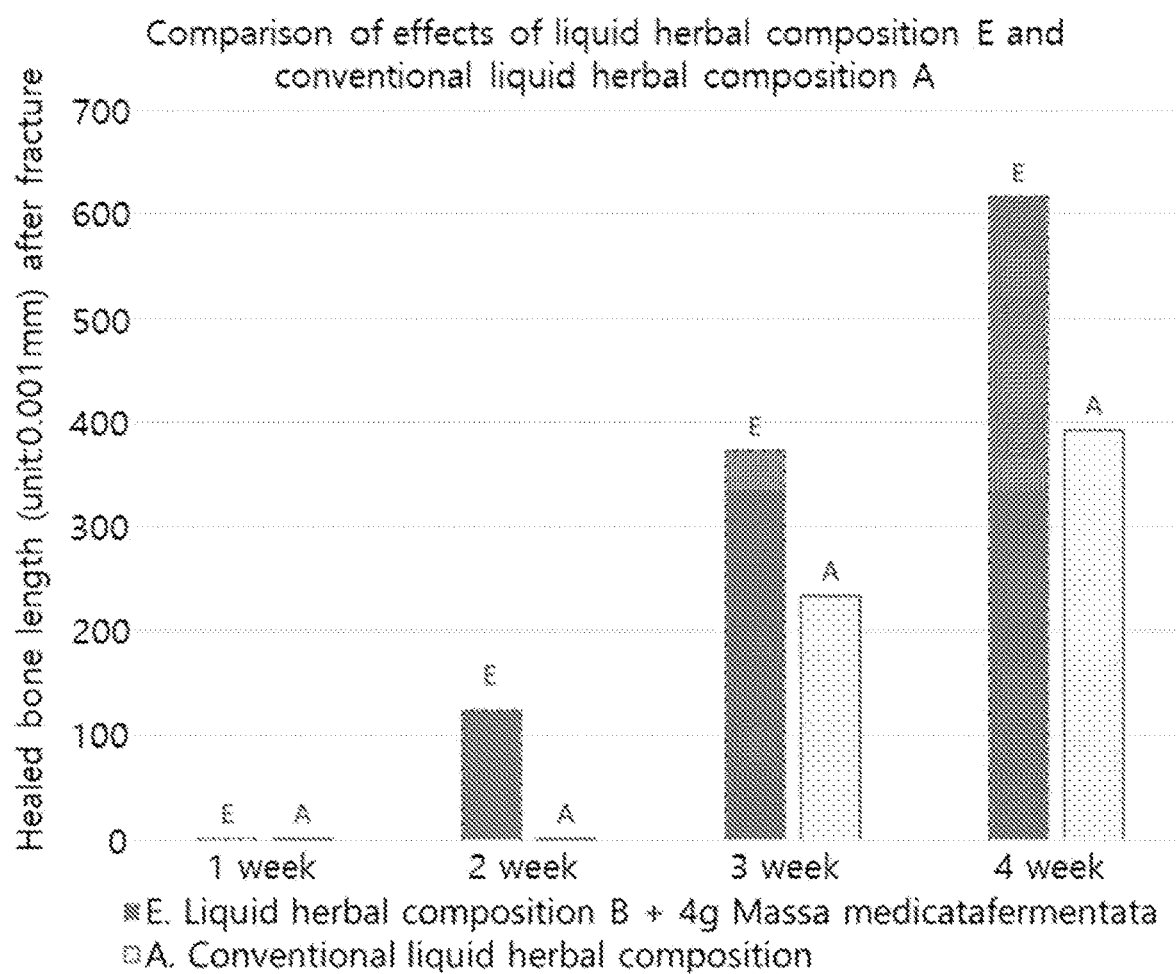

HERBAL COMPOSITION IN POWDER, PILL OR LIQUID FORM FOR SPEEDING UP FRACTURE HEALING AND BONE REGENERATION AND HERBAL FORMULATION IN POWDER, PILL OR LIQUID FORM CONTAINING THE SAME

CROSS-REFERENCE TO RELATED APPLICATION

This application claims priority to Korean Patent Application No. 10-2021-0096593 filed in the Korean Intellectual Property Office on Jul. 22, 2021, the disclosure of which is incorporated by reference herein in its entirety.

BACKGROUND

1. Technical Field

The present invention relates to an herbal composition in powder, pill or liquid form for speeding up fracture healing and bone regeneration and an herbal formulation in powder, pill or liquid form containing the same, and more specifically, to an herbal composition in powder, pill or liquid form for speeding up fracture healing and bone regeneration, which may promote fracture healing and bone regeneration by containing medicinal herbs capable of improving fracture healing and bone regeneration and medicinal herbs capable of enhancing digestion and absorption, and an herbal formulation in powder, pill or liquid form containing the same.

2. Related Art

As used herein, the term "fracture" refers to a phenomenon in which bones in a part of the body are destroyed. This fracture can be healed when two separate bones are joined by the formation of new tissue around the fracture due to the influences of various physical and biological factors.

In recent years, various methods for promoting fracture healing have been proposed, and examples thereof include a method of slowing venous blood flow, a method of stimulating sympathetic nerves, a method of applying electrical stimulation, a method of administering hormones, or methods of administering specific compounds, for example, vitamin D, vitamin D derivatives, BMP, and the like.

However, a satisfactory fracture healing method or fracture healing agent has not yet been developed.

Meanwhile, a healing method for bone fracture caused by a physical external force comprises performing a surgical operation and then fixing the bone with a splint or a plaster bandage so that the bone fracture is naturally healed. However, this healing method has a problem in that the fracture healing period is long.

To overcome this problem, the present applicant disclosed, in Korean Patent No. 10-0731160, an herbal composition for promoting fracture healing containing 18 to 23 wt % of *Angelica gigas*, 18 to 23 wt % of *Cnidium officinale*, 7.5 to 9.5 wt % of *Astragalus membranaceus*, 7.5 to 9.5 wt % of ginseng, 7.5 to 9.5 wt % of *Lycium chinense*, 7.5 to 9.5 wt % of *Codonopsis pilosula*, 3.5 to 4.5 wt % of *Cuscuta chinensis*, 3.5 to 4.5 wt % of *Dipsaci radix*, 3.5 to 4.5 wt % of *Dendrobium moniliforme*, 3.5 to 4.5 wt % of *Psoralea corylifolia*, 3.5 to 4.5 wt % of *Albizziae cortex*, and 3.5 to 4.5 wt % of velvet antler.

However, although the herbal composition has an effect of promoting fracture healing, but it contains only medicinal herbs known to be effective in fracture healing, and thus has the problem of causing indigestion, digestive disorder, etc.

PRIOR ART DOCUMENTS (Patent Document 01) Korean Patent No. 10-0731160
(Patent Document 02) Korean Patent No. 10-0684916

SUMMARY

The present invention has been made in order to solve the above-described problems, and an object of the present invention is to provide an herbal composition in powder, pill or liquid form for speeding up fracture healing and bone regeneration, which contains specific medicinal herbs known to be effective in bone healing and bone regeneration as well as medicinal herbs capable of enhancing digestion, and thus has an enhanced ability to be digested and absorbed and may promote the healing of fracture sites while allowing the medicinal herbal ingredients to be absorbed quickly in the body when taken, and an herbal formulation in powder, pill or liquid form containing the herbal composition.

To achieve the above object, the present invention provides an herbal composition in powder, pill or liquid form for speeding up fracture healing and bone regeneration containing 20 parts by weight of *Angelica gigas*, 16 parts by weight of *Dendrobium moniliforme*, 12 parts by weight of *Dipsaci radix*, 10 parts by weight of antler, 8 parts by weight of *Cnidium officinale*, 8 parts by weight of *Astragalus membranaceus*, and 4 parts by weight of *Achyranthes japonica*.

The present invention also provides an herbal composition in powder, pill or liquid form for speeding up fracture healing and bone regeneration containing 20 parts by weight of *Angelica gigas*, 16 parts by weight of *Dendrobium moniliforme*, 12 parts by weight of *Dipsaci radix*, 10 parts by weight of antler, 8 parts by weight of *Cnidium officinale*, 8 parts by weight of *Astragalus membranaceus*, 4 parts by weight of *Achyranthes japonica*, and 2 parts by weight of *Massa medicata fermentata*.

The present invention also provides an herbal composition in powder, pill or liquid form for speeding up fracture healing and bone regeneration containing 10 parts by weight of *Angelica gigas*, 8 parts by weight of *Dendrobium moniliforme*, 6 parts by weight of *Dipsaci radix*, 5 parts by weight of antler, 4 parts by weight of *Cnidium officinale*, 4 parts by weight of *Astragalus membranaceus*, 2 parts by weight of *Achyranthes japonica*, and 4 parts by weight of *Massa medicata fermentata*.

The present invention also provides an herbal composition in powder, pill or liquid form for speeding up fracture healing and bone regeneration containing 20 parts by weight of *Angelica gigas*, 16 parts by weight of *Dendrobium moniliforme*, 12 parts by weight of *Dipsaci radix*, 10 parts by weight of antler, 8 parts by weight of *Cnidium officinale*, 8 parts by weight of *Astragalus membranaceus*, 4 parts by weight of *Achyranthes japonica*, and 4 parts by weight of *Massa medicata fermentata*.

The effects of the present invention are as follows. Since the herbal composition of the present invention contains *Angelica gigas*, *Dendrobium moniliforme*, *Dipsaci radix*, antler, *Cnidium officinale*, *Astragalus membranaceus*, and *Achyranthes japonica*, which are effective in fracture healing and bone regeneration, as well as *Massa medicata fermentata* capable of enhancing digestion, it has an enhanced ability to be digested and absorbed, and when a patient in need of fracture healing takes the herbal composition, the medicinal herbal ingredients may be absorbed quickly into the body and promote healing of the fracture site, thereby greatly shortening the fracture healing period. In addition, since the composition of the present invention is prepared in powder, pill or liquid form, it may be easily and conveniently taken by the patient.

BRIEF DESCRIPTION OF THE DRAWINGS

FIG. 15 is a graph showing the length of the callus formed at the fracture line in each of the control group and the herbal composition-administered groups.

FIG. 16 is a graph comparing the effects of herbal composition E according to Example 4 and herbal composition A according to Comparative Example 1.

DETAILED DESCRIPTION

Figure 1:
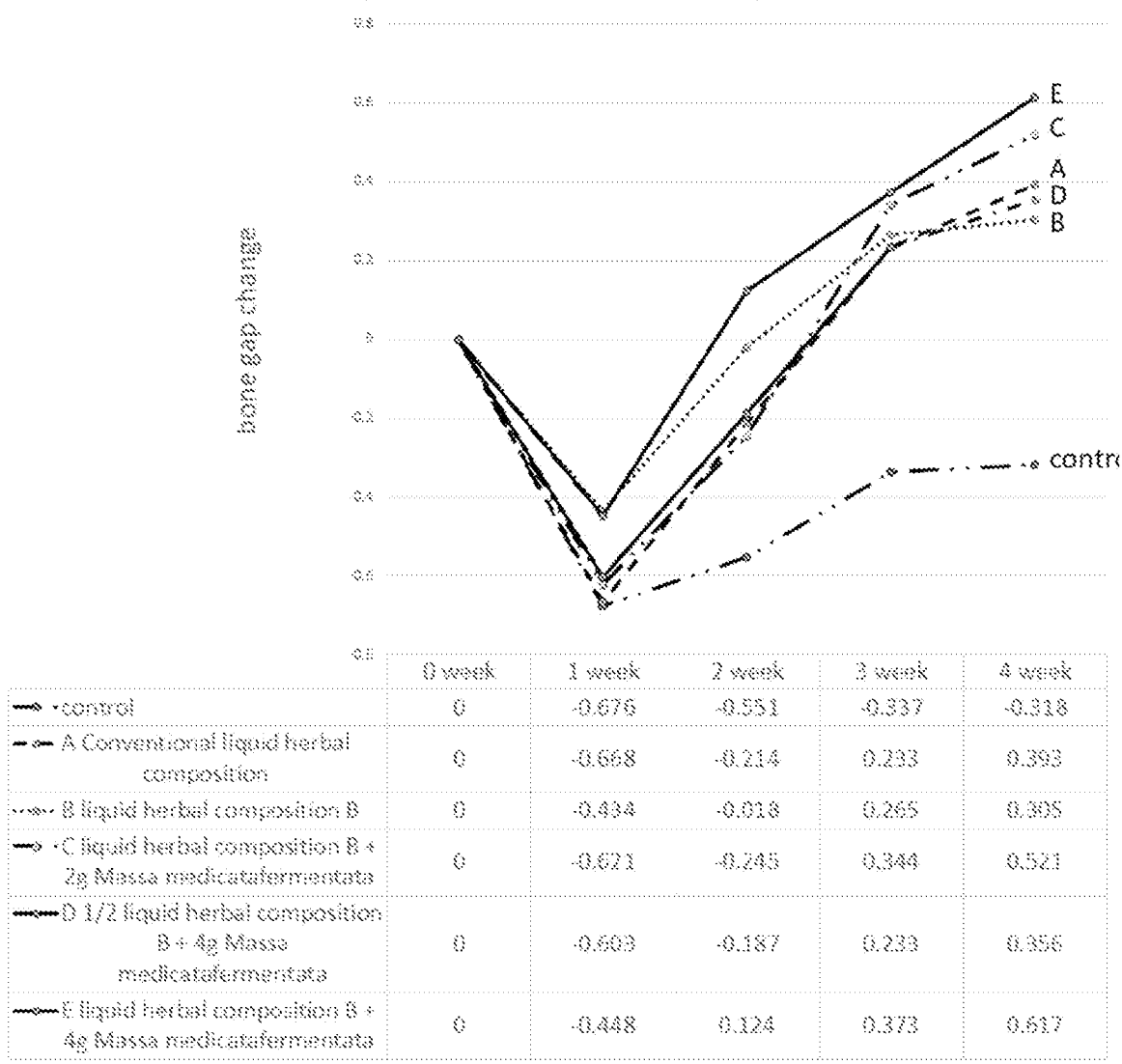
FIG. 1 is a graph showing post-surgical bone gap changes for a control group to which the liquid herbal composition of the present invention was not administered, and groups (Comparative Example 1 and Examples 1 to 4) to which the herbal composition was administered.

An herbal composition in powder, pill or liquid form for speeding up fracture healing and bone regeneration according to one embodiment of the present invention contains 20 parts by weight of *Angelica gigas*, 16 parts by weight of *Dendrobium moniliforme*, 12 parts by weight of *Dipsaci radix*, 10 parts by weight of antler, 8 parts by weight of *Cnidium officinale*, 8 parts by weight of *Astragalus membranaceus*, and 4 parts by weight of *Achyranthes japonica*.

An herbal composition in powder, pill or liquid form for speeding up fracture healing and bone regeneration according to another embodiment of the present invention contains 20 parts by weight of *Angelica gigas*, 16 parts by weight of *Dendrobium moniliforme*, 12 parts by weight of *Dipsaci radix*, 10 parts by weight of antler, 8 parts by weight of *Cnidium officinale*, 8 parts by weight of *Astragalus membranaceus*, 4 parts by weight of *Achyranthes japonica*, and 2 parts by weight of *Massa medicata fermentata*.

An herbal composition in powder, pill or liquid form for speeding up fracture healing and bone regeneration according to still another embodiment of the present invention contains 10 parts by weight of *Angelica gigas*, 8 parts by weight of *Dendrobium moniliforme*, 6 parts by weight of *Dipsaci radix*, 5 parts by weight of antler, 4 parts by weight of *Cnidium officinale*, 4 parts by weight of *Astragalus membranaceus*, 2 parts by weight of *Achyranthes japonica*, and 4 parts by weight of *Massa medicata fermentata*.

An herbal composition in powder, pill or liquid form for speeding up fracture healing and bone regeneration according to yet another embodiment of the present invention contains 20 parts by weight of *Angelica gigas*, 16 parts by weight of *Dendrobium moniliforme*, 12 parts by weight of *Dipsaci radix*, 10 parts by weight of antler, 8 parts by weight of *Cnidium officinale*, 8 parts by weight of *Astragalus membranaceus*, 4 parts by weight of *Achyranthes japonica*, and 4 parts by weight of *Massa medicata fermentata*.

The present invention also provides an herbal formulation which contains, as an active ingredient, the herbal composition in powder, pill or liquid form for speeding up fracture healing and bone regeneration according to the present invention, and is prepared in powder, pill or liquid form.

Hereinafter, preferred embodiments of the present invention will be described in detail.

The *Angelica gigas* of the present invention, which can speed up fracture and bone regeneration, has the effects of nourishing the blood, relieving pain by activating blood circulation, and increasing intestinal energy absorption, and is used for symptoms, such as syndrome of heart-liver blood deficiency, menstrual pain caused by abnormal menstrual cycle, menopause, afterpain, contusion injury, pain caused by a large abscess, and constipation. The effect of *Angelica gigas* on the proliferation of human bone cells was already reported (Clinica Chimica Acta 324 (2002) 89-97, Effect of *Angelica sinensis* on the proliferation of human bone cells).

As *Angelica gigas* having such effects, the *Angelica gigas* root collected in the fall is used in a dry state. The content of *Angelica gigas* is preferably 15 to 30 wt % based on the total weight of the herbal composition. If the content of *Angelica gigas* in the herbal composition is excessively high, problems of edema and diarrhea may arise.

*Dendrobium moniliforme* that is used in the present invention is an evergreen perennial grass belonging to the family Orchidaceae, is about 20 cm in height, and lives attached to rocks or old trees, and a lot of thick roots sprout from the rhizome. Several stems come out and grow straight, and the old ones have no leaves on the stems and have only nodes. The leaves are 2 to 3 years old, come out alternately, and are 4 to 7 cm in length and about 1 cm in width.

*Dendrobium moniliforme* has the effects of promoting the secretion of gastric juice by strengthening the stomach, and removing fever by cultivating yin energy, and is used to treat symptoms such as thirst caused by fever, fever caused by weak yin, and lack of strength in the back and knees. In addition, *Dendrobium moniliforme* acts selectively on the Kidney meridian to strength the kidney and bone.

If the content of *Dendrobium moniliforme* in the herbal composition is excessively high, a problem of fever may arise. Thus, the content of *Dendrobium moniliforme* is preferably 15 to 20 wt % based on the total weight.

The term "*Dipsaci radix*" refers to the root of *Dipsacus asperoides* C. Y. Cheng et T. M. Ai which is a perennial herb belonging to the family Dipsacaceae. *Dipsaci radix* is a kind of food and herbal medicine that has been used by people since ancient times. In recent years, as the effects of *Dipsaci radix* on growth hormone secretion and growth promotion have been revealed, the demand has gradually expanded, and research on the safety and efficacy thereof has been actively conducted.

*Dipsaci radix* has the effects of strengthening the liver and kidney and connecting broken bones or muscles, and is used to treat symptoms such as the lack of proper blood of the liver and kidney, back and leg pain, bleeding from the uterus during pregnancy, and a disease in which muscles (tendons) are damaged and bones are broken.

The known pharmacological actions of *Dipsaci radix* include antidiabetic effects, muscle and joint pain alleviation action, anticomplement effects, treatment of cough asthma caused by decreased physical strength, and treatment of diarrhea. Continuous research on the new efficacy of *Dipsaci radix* extracts is in progress in various fields.

As *Dipsaci radix* in the present invention, one obtained by harvesting and drying the roots of *Dipsacus asperoides* C. Y. Cheng et T. M. Ai and removing the hair and beard from the roots is used. The content of *Dipsaci radix* is 10 to 15 wt % based on the total weight of the herbal composition. If the content of *Dipsaci radix* is excessively high, a problem of fever may arise.

The antler that is used in the present invention is obtained by cutting and drying the ossified horns of *Cervus nippon* Temminck, *Cervus elaphus* Linne or *Cervus canadensis* Erxleben belonging to the family Cervidae. The antler has the effects of nourishing the vitality of the kidneys, boosting yang energy, promoting bone growth by promoting the synthesis of proteins and nucleic acids, promoting growth, promoting hematopoiesis, and strengthening the heart, and is known to improve immune function and to be effective against liver disease and osteoporosis.

If the content of the antler is excessively high, a problem of diarrhea may arise. Thus, the content of the antler is preferably 10 to 15 wt % based on the total weight of the herbal composition.

*Cnidium officinale* that is used in the present invention is a perennial dicotyledonous plant belonging to the family Umbelliferae, and is native to China. It has the effects of facilitating blood circulation, helping the operation of Qi smoothly, removing gout, and stopping pain, and is used to treat symptoms such as menstrual irregularities, menopause menstrual pain, pain after difficult delivery, quadriplegia, contusion injury, and headache.

As *Cnidium officinale* having such effects, one obtained by collecting the root in September through November, removing the small branches and then drying the root is used. The content of *Cnidium officinale* is preferably 5 to 10 wt % based on the total weight of the herbal composition. If the content of *Cnidium officinale* in the herbal composition is excessively high, a problem of fever may arise. It is considered that, although *Cnidium officinale* does not exert a direct effect on fractures, it further promotes fracture healing by exhibiting the effect of treating inflammation by the action of circulating blood circulation.

*Astragalus membranaceus* that is used in the present invention is a medicinal herb that protects the functions of the skin, prevents sweating, gives new flesh, and helps the immune function.

*Astragalus membranaceus* has the effects of nourishing qi, boosting yang qi, protecting and firming the skin, removing toxins such as inflammation, giving new flesh, facilitating moisture drainage, and removing edema, and is used to treat symptoms such as spleen Gi deficiency, symptom of sunken middle qi, symptoms of weakness in both the nasal and lungs, a condition in which the body is weak and has no energy, excessive sweating, a big boil, weakness or lack of energy, and hydropsy.

*Astragalus membranaceus* is a good medicinal herb for obese people, because it controls the amount of sweat and is used as a treatment for diabetes due to its diuretic action.

Whole body sweating, dizziness and exhaustion are evidence that the qi has become weak. In addition to these symptoms, *Astragalus membranaceus* is also effective for boredom and lethargy. *Astragalus membranaceus* has the effects of suppressing sweating, strengthening the skin, draining pus, alleviating swelling, and giving new flesh. In addition, it relieves chronic fatigue and is effective in improving insomnia and weak constitution. It contains alkaloids, amino acids, aspartic acid, and the like. It is sweet in taste and slightly warm in nature. It acts on nasal meridian, lung meridian, triple energizer meridian, and nerve. *Astragalus membranaceus* strengthens Qi and acts as a tonic and cardiac tonic.

*Astragalus membranaceus* helps blood circulation due to its vasodilation action, and increases the resistance of capillaries. As *Astragalus membranaceus* in the present invention, the 2-5 year-old root collected in the fall or spring is used after drying of the peel. In the present invention, *Astragalus membranaceus* known to have the above-described effects is added in order to allow a bone fracture in the human body to be healed more quickly through the effect of strengthening energy in fracture healing.

As *Astragalus membranaceus*, the rood collected in spring and autumn is used after drying and removal of the beard and hair from the root. If the content of *Astragalus membranaceus* in the herbal composition is excessively high, a problem of indigestion or fever may arise. Thus, the content of *Astragalus membranaceus* is preferably 5 to 10 wt % based on the total weight of the herbal composition.

*Achyranthes japonica* that is used in the present invention has a node having a shape similar to that of a cow's knee in the plant stem. *Achyranthes japonica* is a medicinal herb corresponding to the Achyranthes root, and contains saponin and a large amount of calcium as active ingredients, and is known to have a remarkable effect on the treatment of knee diseases (arthritis, rheumatoid arthritis, and inflammation caused by bruises). It is also frequently used in the case in which the waist and legs feel heavy and are painful and sometimes when there are muscle spasms. In addition, *Achyranthes japonica* is also used to relieve cerebral blood vessel spasms while lowering blood pressure when there are symptoms such as headache, dizziness, and eye irritation in hypertension. Young shoots thereof are eaten as herbs, and the root is also used for neuralgia in folk remedy.

If the content of *Achyranthes japonica* in the herbal composition is excessively high, it may cause diarrhea. Thus, the content of *Achyranthes japonica* is preferably 2 to 5 wt % based on the total weight of the herbal composition.

As used herein, "*Massa medicata fermentata*" in oriental medicine refers to a medicinal herb made by mixing wheat flour, bran, cocklebur juice, *Glycine soja* juice, Sweet annie juice, Apricot kernel extract, red bean paste, etc. and fermenting the mixture together with yeast. It is known that *Massa medicata fermentata* mainly acts on the spleen and stomach to strengthen the function of the digestive system, has an action to comfort the stomach with the action to help digestion, and exhibits effects against an upset stomach, a stuffy chest, vomiting and diarrhea, and abdominal pain due to extravasated blood after childbirth

*Massa medicata fermentata* serves to enhance the digestion of the herbal composition by the above-mentioned efficacy, thereby improving the absorption of the herbal composition when taken, so that the effects of the medicinal herbs can be quickly obtained. If the content of *Massa medicata fermentata* is excessively low, it may be difficult to obtain the efficacy of *Massa medicata fermentata*. If the content of *Massa medicata fermentata* is excessively high, it may cause drowsiness. Thus, the content of *Massa medicata fermentata* is preferably 2 to 5 wt % based on the total weight of the herbal composition.

Comparative Example 1 (Liquid Herbal Composition A: Korean Patent Application No. 10-0731160 Filed in the Name of this Applicant)

Medicinal herbs in an amount corresponding to 10 packs, each consisting of 20 g of *Angelica gigas,* 20 g of *Cnidium*

*officinale*, 8 g of ginseng, 8 g of *Lycium chinense*, 8 g of *Codonopsis pilosula*, 4 g of *Dipsaci radix*, 4 g of *Dendrobium moniliforme*, 4 g of *Psoralea coryhfoha*, 4 g of *Cuscuta chinensis*, 4 g of *Albizziae cortex*, and 4 g of antler, were added to 6,000 ml of water and decocted in a pot at 95 to 100° C. for 2 to 4 hours, and the medicinal herbs were filtered out to obtain 1,800 ml of a final liquid herbal composition.

Example 1 (Liquid Herbal Composition B: Base)

Medicinal herbs in an amount corresponding to 10 packs, each consisting of 20 g of *Angelica gigas*, 16 g of *Dendrobium moniliforme*, 12 g of *Dipsaci radix*, 10 g of antler, 8 g of *Cnidium officinale*, 8 g of *Astragalus membranaceus*, and 4 g of *Achyranthes japonica*, were added to 6,000 ml of water and decocted in a pot at 95 to 100° C. for 2 to 4 hours, and the medicinal herbs were filtered out to obtain 1,200 ml of a final liquid herbal composition.

Example 2 (Liquid Herbal Composition C: Liquid Herbal Composition B+2 g of *Massa medicata fermentata*)

A liquid herbal composition having a final volume of 1,200 ml was obtained in the same manner as in Example 2, except that 2 g of *Massa medicata fermentata* was added.

Example 3 (Liquid Herbal Composition D: ½ Liquid Herbal Composition B+4 g of *Massa medicata fermentata*)

Medicinal herbs in an amount corresponding to 10 packs, each consisting of 10 g of *Angelica gigas*, 8 g of *Dendrobium moniliforme*, 6 g of *Dipsaci radix*, 5 g of antler, 4 g of *Cnidium officinale*, 4 g of *Astragalus membranaceus*, 2 g of *Achyranthes japonica*, and 4 g of *Massa medicata fermentata*, were added to 6,000 ml of water and decocted in a pot at 95 to 100° C. for 2 to 4 hours, and the medicinal herbs were filtered out to obtain 1,200 ml of a final liquid herbal composition.

Example 4 (Herbal Composition E: Herbal Composition B+4 g of *Massa medicata fermentata*)

Medicinal herbs in an amount corresponding to 10 packs, each consisting of 20 g of *Angelica gigas*, 16 g of *Dendrobium moniliforme*, 12 g of *Dipsaci radix*, 10 g of antler, 8 g of *Cnidium officinale*, 8 g of *Astragalus membranaceus*, 4 g of *Achyranthes japonica*, and 4 g of *Massa medicata fermentata*, were added to 6,000 ml of water and decocted in a pot at 95 to 100° C. for 2 to 4 hours, and the medicinal herbs were filtered out to obtain 1,200 ml of a final liquid herbal composition.

As in Examples 1 to 4, the herbal composition of the present invention is preferably prepared in liquid form and taken as a liquid, but is not limited thereto and may also be prepared in powder or pill form. The herbal composition in pill form may be prepared by preparing the herbal composition in liquid form, extracting the herbal composition with hot water or ethanol, concentrating and drying the extract, and forming the dried extract into a pill. The herbal composition in powder form may be prepared by powdering the pill. However, the method of preparing the herbal composition of the present invention in liquid, powder or pill form is not critical to the present invention, and detailed description thereof will be omitted herein.

Experimental Example 1

In order to examine whether liquid herbal formulations A, B, C, D and E obtained in Comparative Example 1 and Examples 1 to 4 above would speed up bone fracture and bone regeneration, an experiment was performed under the following conditions.

1. Experimental Method

In order to examine the effect of each of the liquid herbal compositions on bone healing, water and each of the liquid herbal compositions were administered to 7-week-old SD rats with fractures, and then X-ray imaging was performed.

The administration frequency and dose of each test substance for each group are as follows.

Group control: vehicle control (water)
Group A: liquid herbal composition A (10 ml/kg p.o)
Group B: liquid herbal composition B (10 ml/kg p.o)
Group C: liquid herbal composition C (10 ml/kg p.o)
Group D: liquid herbal composition D (10 ml/kg p.o)
Group E: liquid herbal composition E (10 ml/kg p.o)

2. Measurement

1) Measurement of Bone Regeneration Rate

Water and each of liquid herbal compositions A, B, C, D and E were administered orally every day to the experimental animals of each group, and to examine the bone regeneration speed, X-ray imaging was performed weekly to measure the ulnar gap.

2) Measurement of Callus Formation Rate

After oral administration of liquid herbal composition A, B, C, D or E for 4 weeks, 2 mm portions with respect to the ulnar fracture line were extracted and subjected to H & E staining. The length of the callus regenerated from the fracture line was measured by observing the stained area with an Olympus microscope.

3. Experimental Results

1) Effect of Liquid Herbal Composition A, B, C, D or E on Bone Regeneration

After fracture induction, liquid herbal composition A, B, C, D or E was administered p.o. daily at a dose of 10 ml/kg p.o, and X-ray imaging was performed to measure the ulnar gap. The results are shown in FIGS. 1 and 3 to 8.

Figure 2:
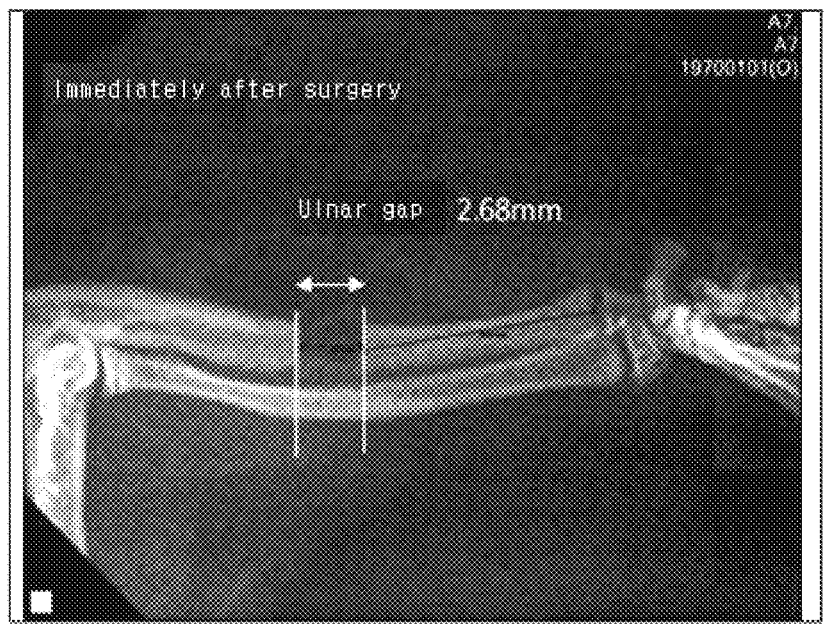
FIG. 2 shows X-ray photographs used to calculate the speed of bone regeneration after administration of the herbal composition of the present invention following fracture surgery.
Figure 2:
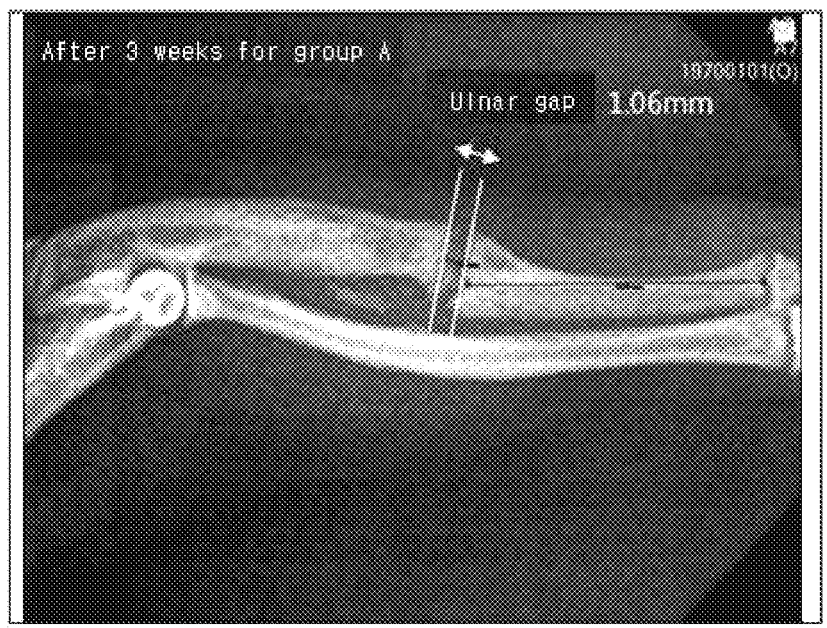
Figure 3:
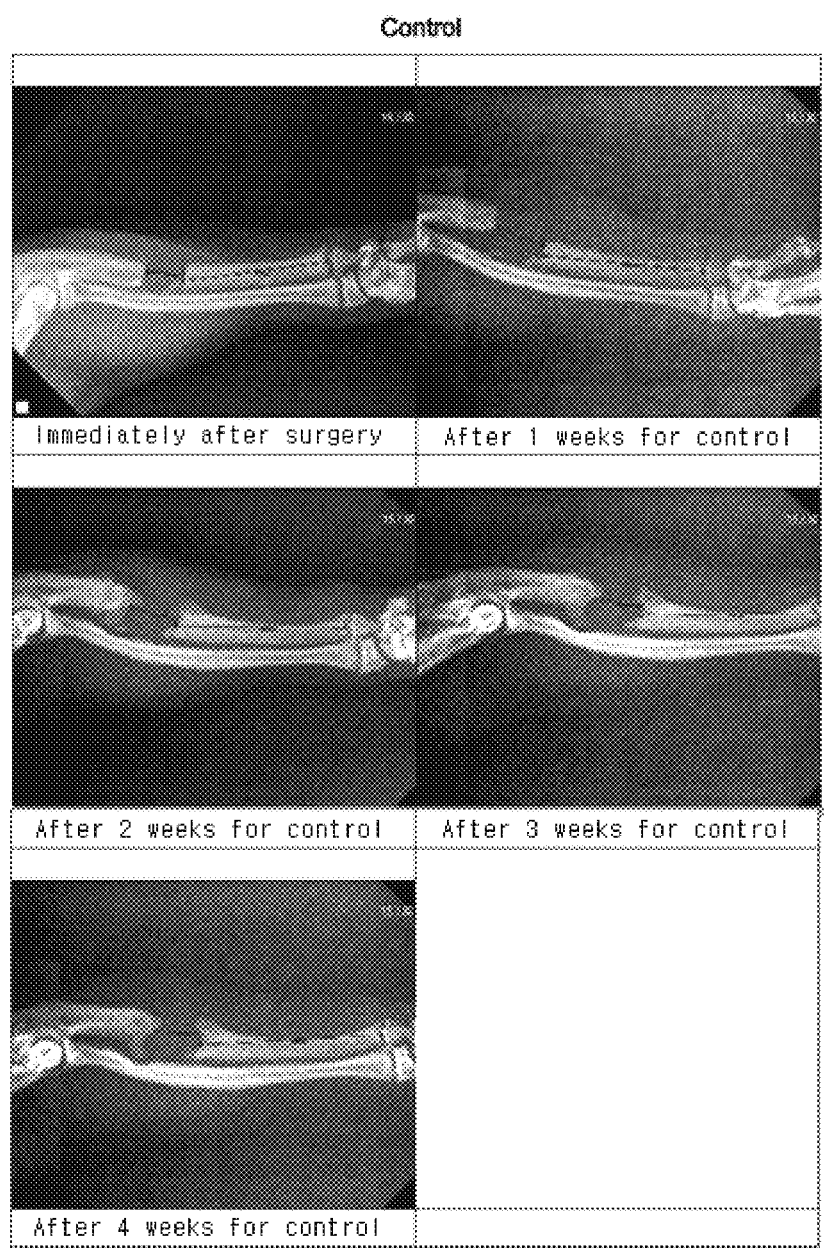
FIGS. 3, 4, 5, 6, 7, and 8 are X-ray photographs of the control group after fracture surgery, and X-ray photographs of the herbal composition-administered group before and after administration of the herbal composition after fracture surgery.
Figure 4:
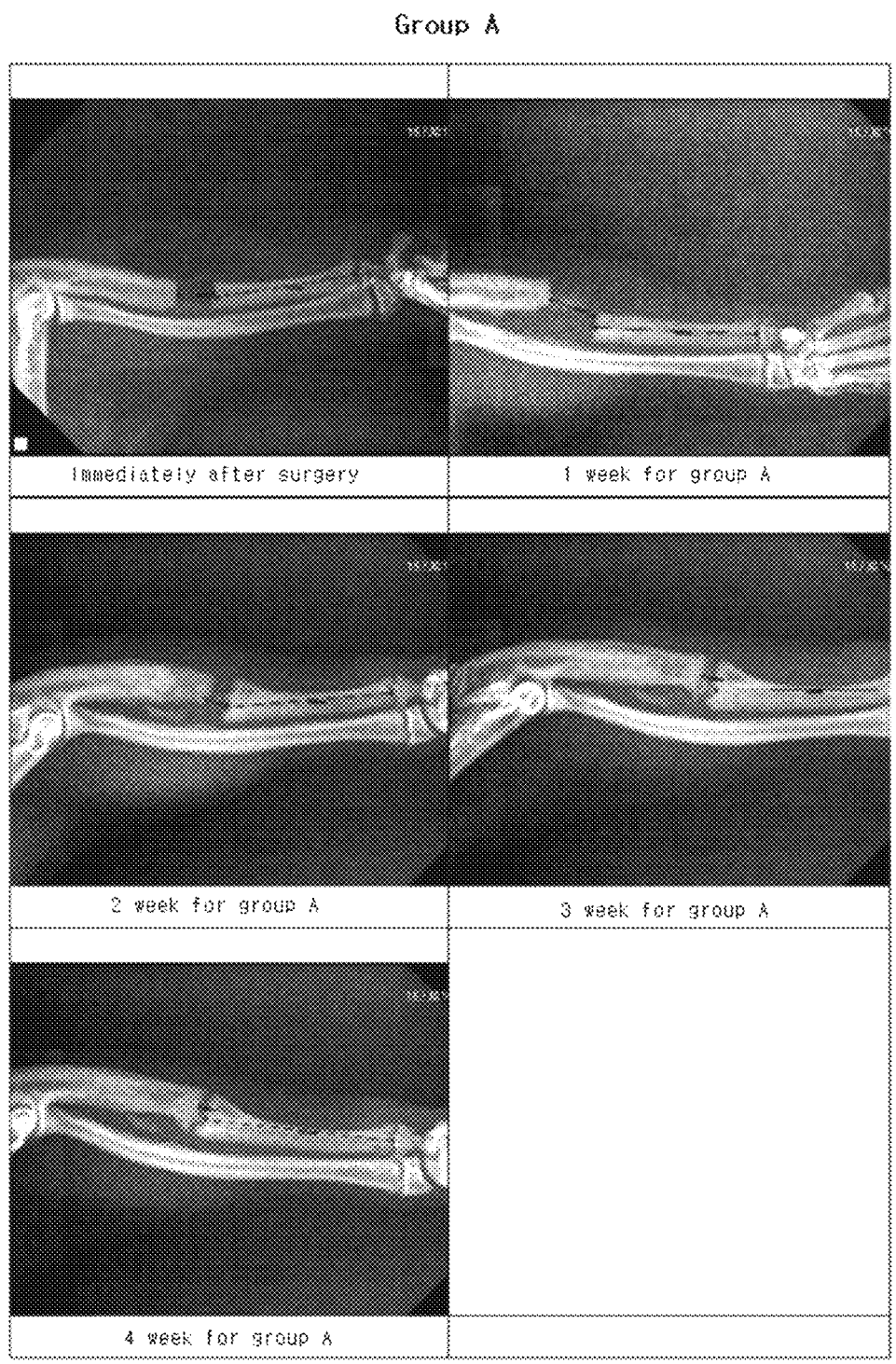
Figure 5:
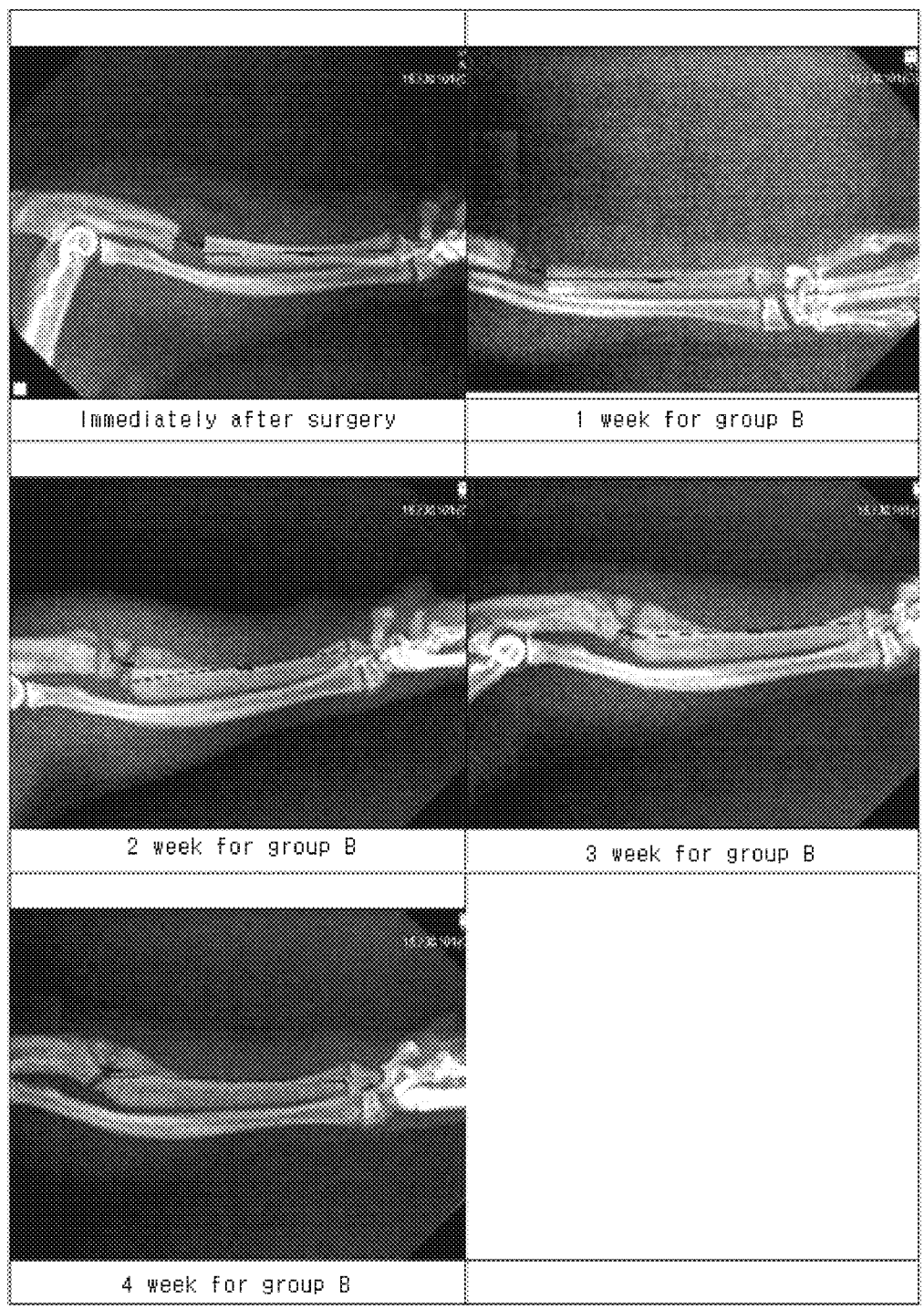
Figure 6:
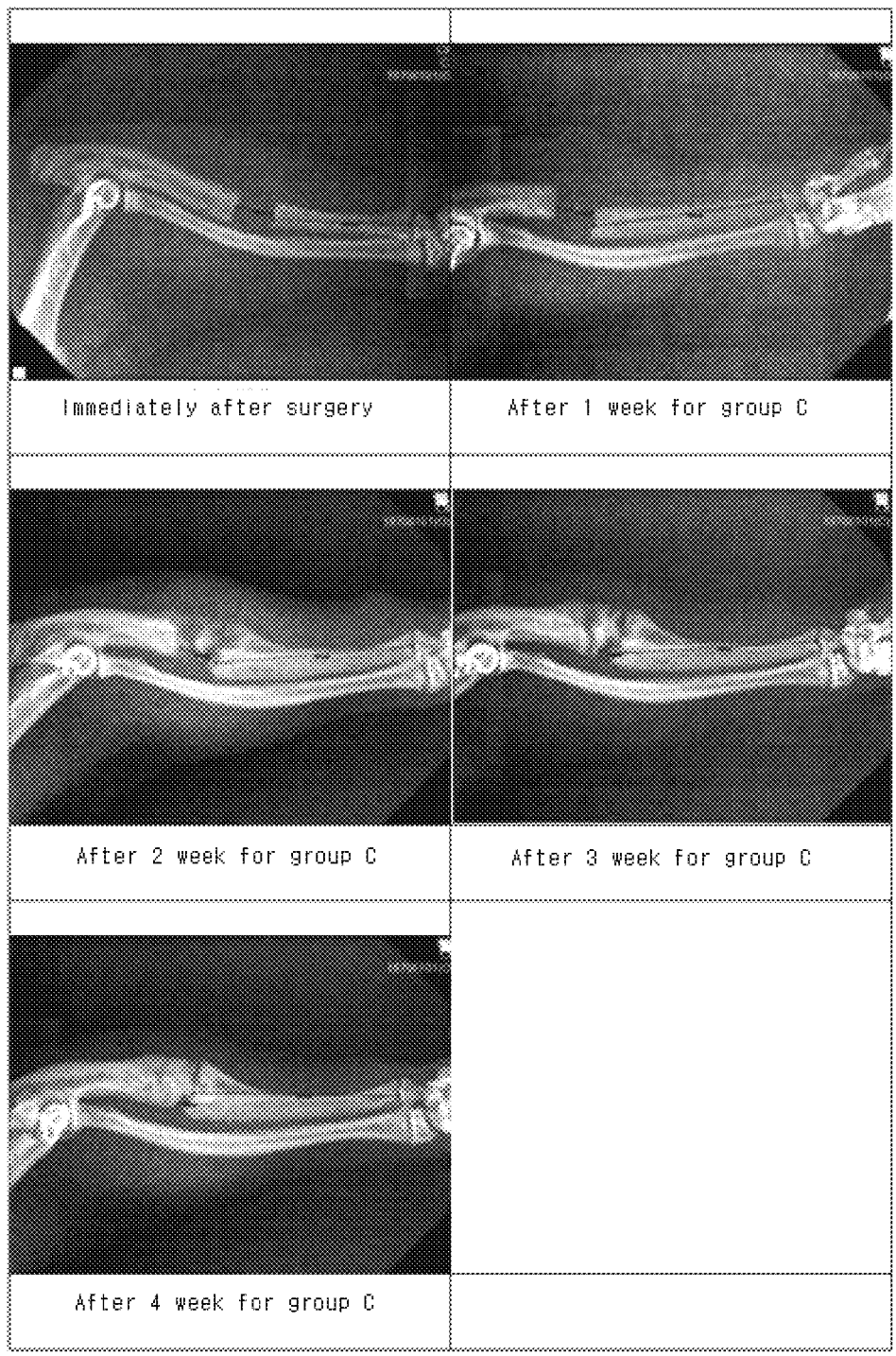
Figure 7:
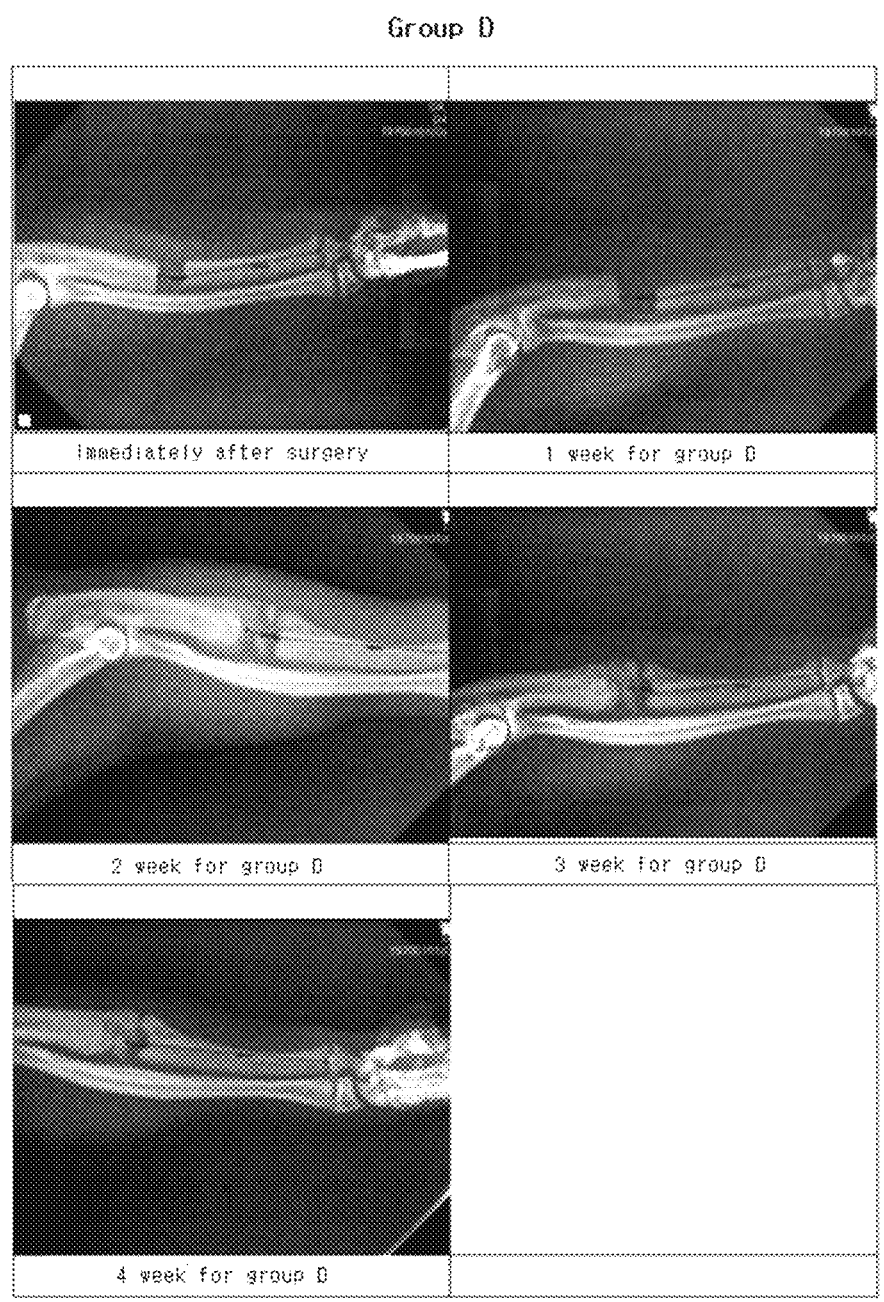
Figure 8:
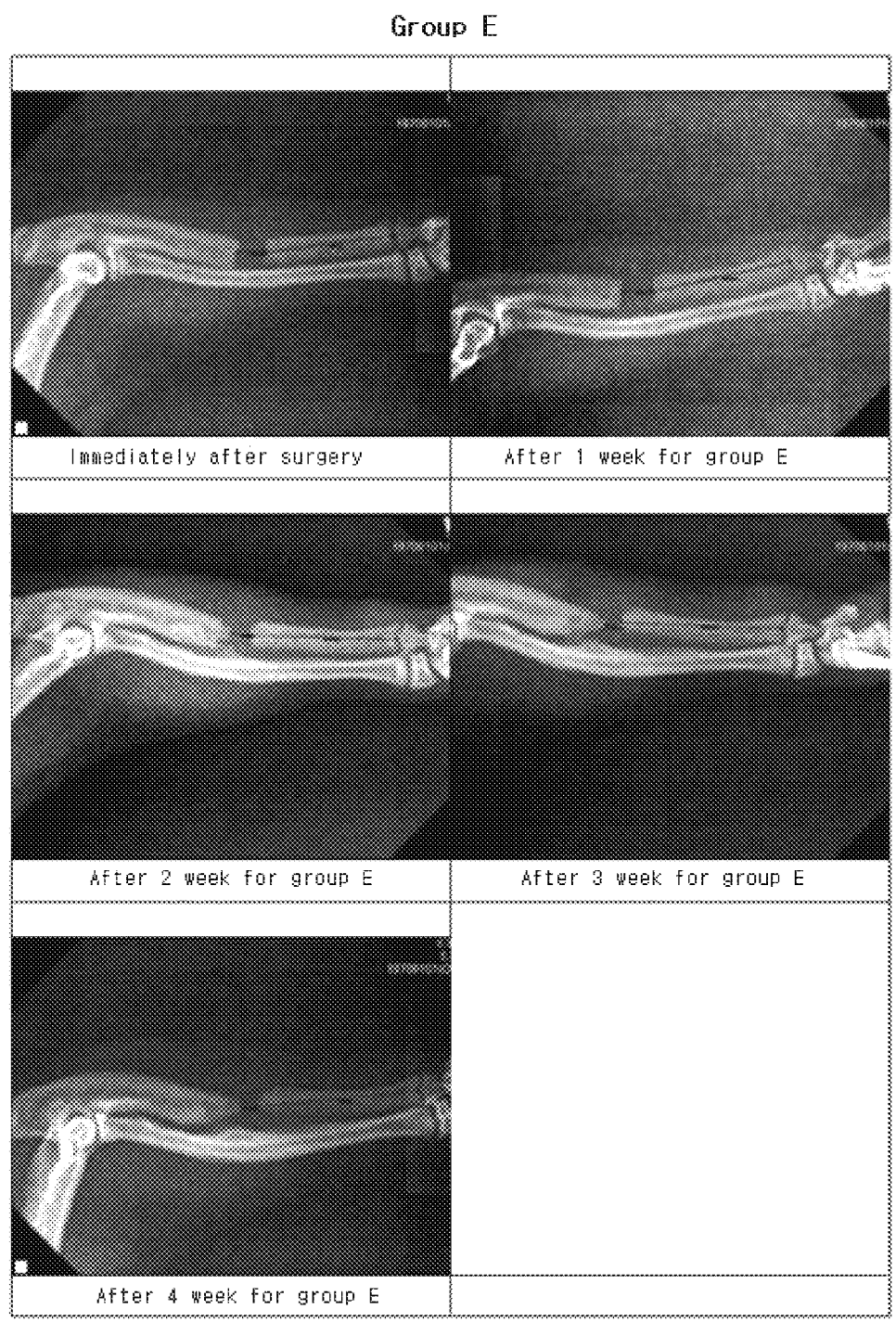
Figure 9:
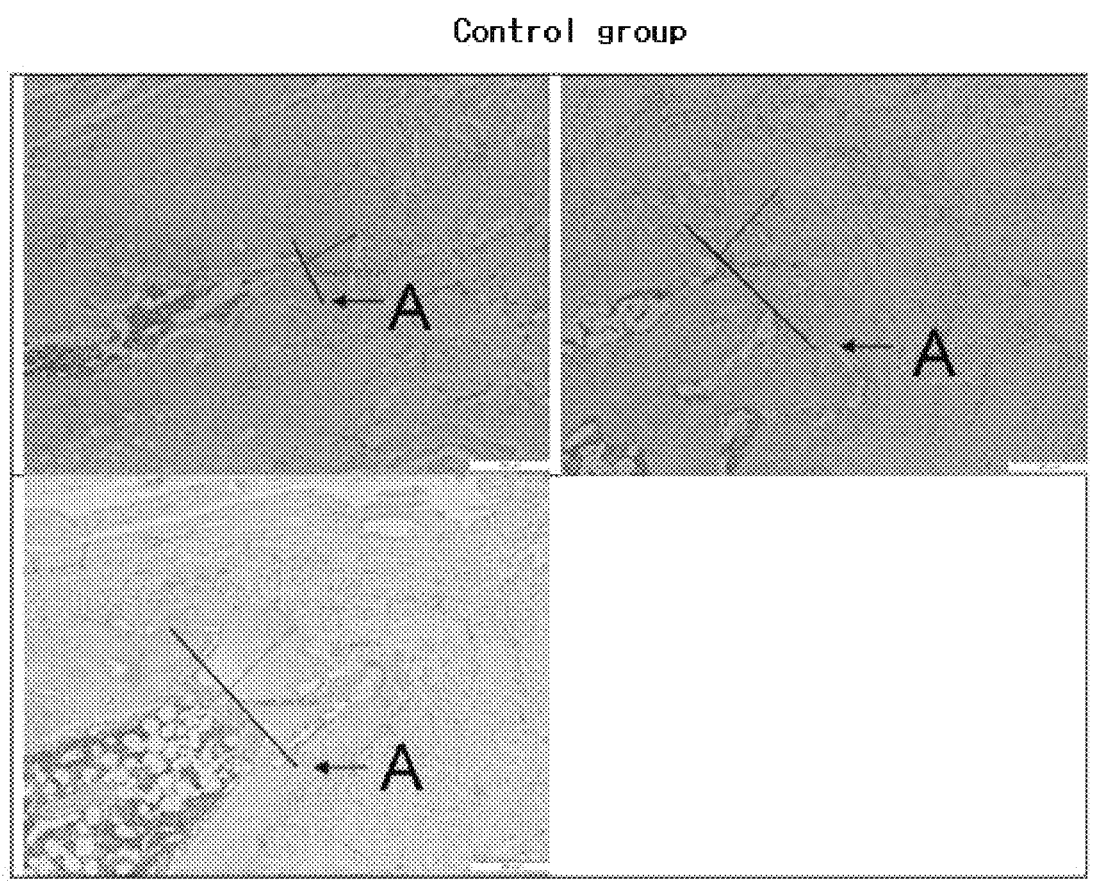
FIGS. 9, 10, 11, 12, 13, and 14 are representative histological photographs of peri-fracture tissues in the control group and the herbal composition-administered groups.
Figure 10:
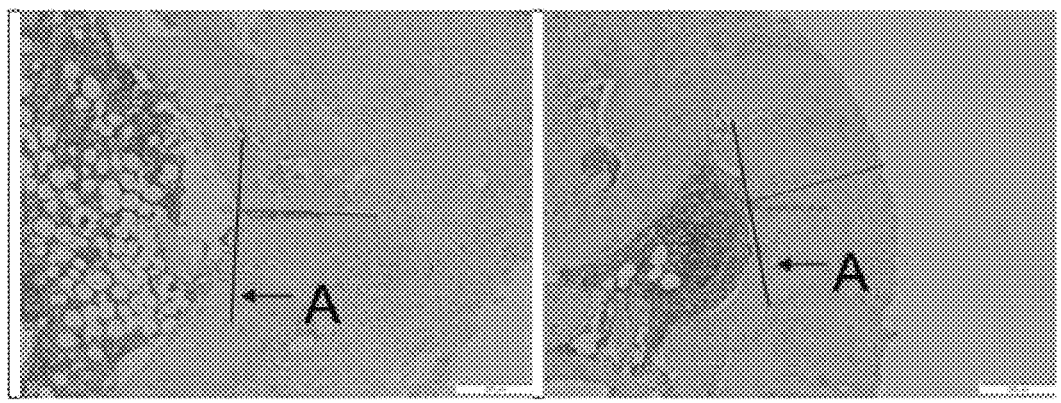
Figure 11:
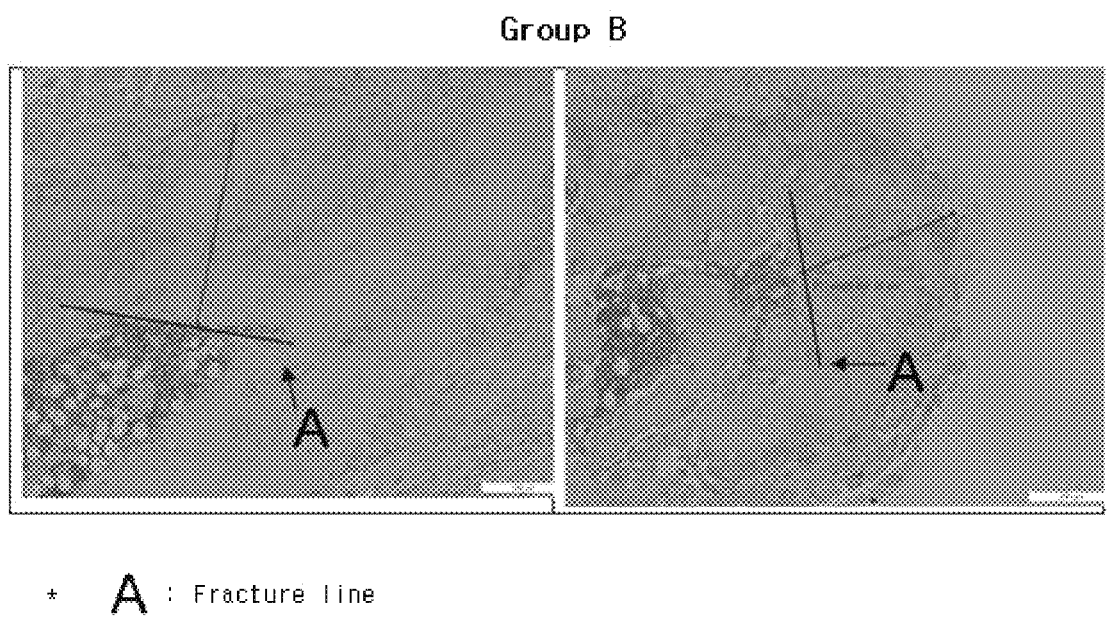
Figure 12:
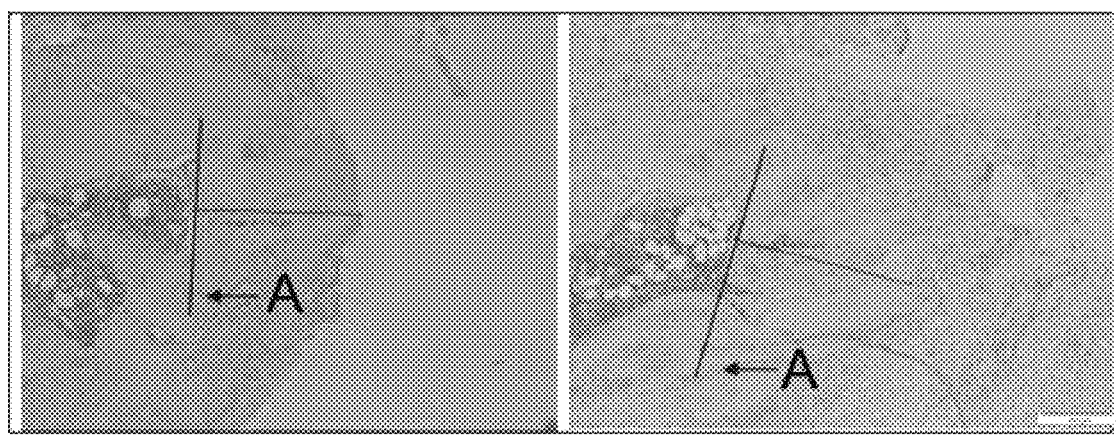
Figure 13:
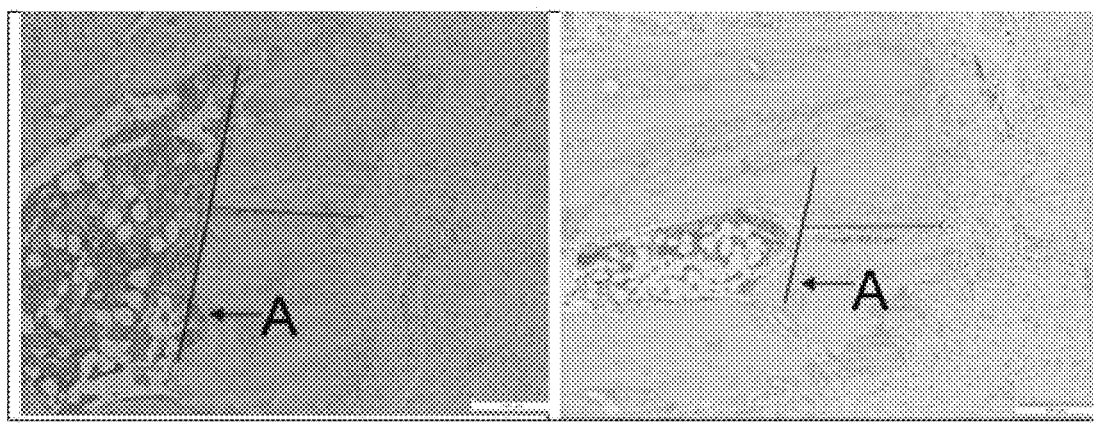
Figure 14:
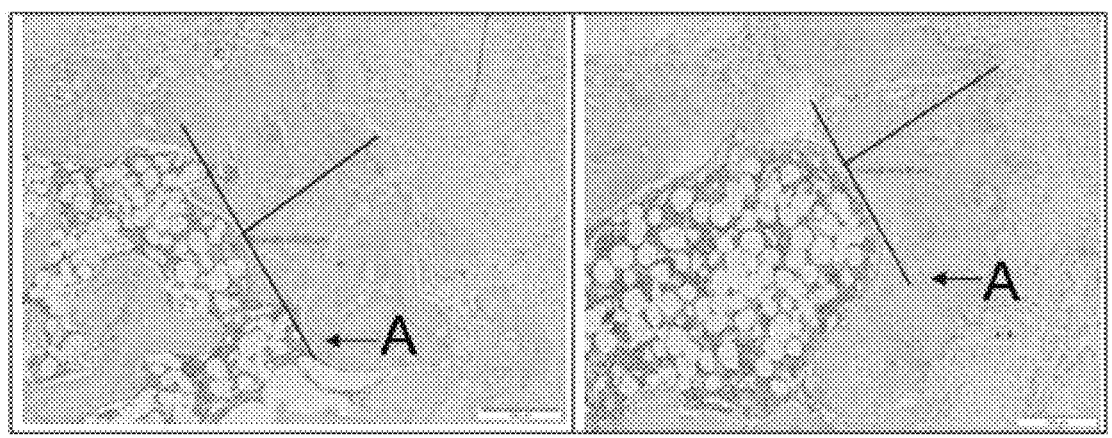

(Method for calculating bone regeneration rate: as shown in FIG. 2, ulnar gap immediately after surgery (2.68 mm)–ulnar gap after 3 weeks (1.06 mm)=1.62 mm. As the callus is formed and bone is regenerated, the value increases.)

As shown in FIG. 1, until 1 week after administration during the experiment, no difference was seen between the groups, but after 2 weeks, the group to which liquid herbal composition E was administered started to show a significant difference from the control group, and after 3 weeks, the groups to which liquid herbal compositions A, B, C, D and E were administered, respectively, all showed significant differences from the control group.

Looking at the experimental results depending on time, the control group showed a bone regeneration rate of −15% at weeks 3 and 4, but the group to which liquid herbal composition E was administered showed increases in bone regeneration rates of 4.7% at week 2, 14.3% at week 3, and 23.6% at week 4. The group to which liquid herbal composition C was administered showed increases in bone regeneration rates of 13.4% at week 3 and 20.5% at week 4; the group to which liquid herbal composition A was administered showed increases in bone regeneration rates of 9.6% at week 3 and 16.3% at week 4; the group to which liquid herbal composition D was administered showed increases in bone regeneration rates of 10.3% at week 3 and 15.7% at week 4; and the group to which liquid herbal composition B was administered showed increases in bone regeneration rates of 10.6% at week 3 and 12.3% at week 4.

2) Results of X-Ray Imaging Before and After Administration of Liquid Herbal Composition FIGS. 3 to 8 show representative X-ray photographs taken every week. As shown therein, it can be seen that bone regeneration was more accelerated in the liquid herbal composition-administered group than in the control group.

3) Representative Histological Photographs of Peri-Fracture Tissues and Length of Callus Formed at Fracture Line FIGS. 9 to 14 show representative histological photographs of peri-fracture tissues, and FIG. 15 is a graph showing the length of the callus formed at the fracture line. As shown therein, it can be seen that the bone (callus) regenerated from the fracture line was formed more in the liquid herbal composition-administered groups than in the control group.

4) Comparison of Effects of Liquid Herbal Composition E and Conventional Liquid Herbal Composition (Comparative Example 1)

As a result of comparing the effect of liquid herbal composition E of Example 4 with the effect of conventional liquid herbal composition A of Comparative Example 1, as shown in the graph in FIG. 16, it can be seen that, in the case of the group to which liquid herbal composition E was administered, bone healing started from 2 weeks after fracture occurrence, and 4 weeks, the bone healing effect of liquid herbal composition E increased by 57% compared to that of liquid herbal composition A.

4. Conclusions

This experiment was performed to examine the effects of liquid herbal compositions A, B, C, D and E on fracture healing and bone regeneration. In this experiment, each liquid herbal composition was administered orally to the experimental animals with fracture, and then X-ray imaging was performed to measure the ulnar gap.

As a result, it could be confirmed that, until 1 week after administration, there was no difference in fracture gap between the groups, but after 2 weeks, the group to which liquid herbal composition E was administered showed a significant difference from the control group, and after 3 weeks, the groups to which liquid herbal compositions A, B, C, D and E, respectively, all showed increased bone regeneration rates compared to the control group.

In particular, it was confirmed that the bone regeneration rates at week 4 decreased by −15% in the control group, but increased by 23.6% in the liquid herbal composition E-administered group, 20.5% in the liquid herbal composition C-administered group, 16.3% in the liquid herbal composition A-administered group, 15.7% in the liquid herbal composition D-administered group, and 12.3% in the liquid herbal composition B-administered group.

From the results of X-ray imaging, it could be seen that bone regeneration was faster in the groups to which liquid herbal compositions A, B, C, D and E, respectively, than in the control group. In addition, from the histological photographs, it could be confirmed that the callus (regenerated bone) was more formed in the groups to which liquid herbal compositions A, B, C, D and E, respectively, than in the control group.

In particular, it could be confirmed that, in the case of the group to which liquid herbal composition E was administered, bone healing started from 2 weeks after fracture occurrence, and 4 weeks, the bone healing effect of liquid herbal composition E increased by 57% compared to that of liquid herbal composition A.

These results show that, in addition to *Angelica gigas, Dendrobium moniliforme, Dipsaci radix*, antler, *Cnidium officinale* and *Astragalus membranaceus, Achyranthes japonica* known to be effective in arthritis treatment and *Massa medicata fermentata* that enhances the digestion and absorption of the herbal ingredients of the liquid herbal composition serve to greatly speed up bone healing and bone regeneration.

In addition, during the first week after inducing a fracture, the bone gap becomes wider due to the activity of osteoclasts. Looking at the values at week 1 in FIG. 1, the experimental groups to which the liquid herbal compositions were administered showed less bad results. This is because the liquid herbal composition inhibited osteoclast activity, and thus it can be seen that the liquid herbal composition can be actively used for the treatment and prevention of osteoporosis.

Although preferred embodiments of the present invention have been disclosed in the present specification and the accompanying drawings and specific terms have been used, these are only used in a general sense to easily explain the technical content of the present invention and to help the understanding of the present invention, and are not intended to limit the scope of the present invention. It will be apparent to those of ordinary skill in the art to which the present invention pertains that, in addition to the embodiments disclosed herein, other modifications based on the technical spirit of the present invention are possible.

What is claimed is:

1. An herbal composition in powder, pill or liquid form for speeding up fracture healing and bone regeneration consisting of 20 parts by weight of *Angelica gigas*, 16 parts by weight of *Dendrobium moniliforme*, 12 parts by weight of *Dipsaci radix*, 10 parts by weight of antler, 8 parts by weight of *Cnidium officinale*, 8 parts by weight of *Astragalus membranaceus*, 4 parts by weight of *Achyranthes*, and 2 parts by weight of *Massa medicata fermentata*.

2. An herbal composition in powder, pill or liquid form for speeding up fracture healing and bone regeneration consisting of 10 parts by weight of *Angelica gigas*, 8 parts by weight of *Dendrobium moniliforme*, 6 parts by weight of *Dipsaci radix*, 5 parts by weight of antler, 4 parts by weight of *Cnidium officinale*, 4 parts by weight of *Astragalus membranaceus*, 2 parts by weight of *Achyranthes*, and 4 parts by weight of *Massa medicata fermentata*.

3. An herbal formulation in powder, pill or liquid form for speeding up fracture healing and bone regeneration, which contains, as an active ingredient, the herbal composition of claim 1, and is prepared in powder, pill or liquid form.

4. An herbal composition in powder, pill or liquid form for speeding up fracture healing and bone regeneration consisting of 20 parts by weight of *Angelica gigas*, 16 parts by weight of *Dendrobium moniliforme*, 12 parts by weight of *Dipsaci radix*, 10 parts by weight of antler, 8 parts by weight of *Cnidium officinale*, 8 parts by weight of *Astragalus membranaceus*, 4 parts by weight of *Achyranthes*, and 4 parts by weight of *Massa medicata fermentata*.

* * * * *